US00PP16642P2

(12) United States Plant Patent
Utecht

(10) Patent No.: US PP16,642 P2
(45) Date of Patent: Jun. 13, 2006

(54) ***GERANIUM* PLANT NAMED 'GRASALM'**

(50) Latin Name: *Pelargonium zonale*
Varietal Denomination: Grasalm

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 83 days.

(21) Appl. No.: 10/998,665

(22) Filed: Nov. 30, 2004

(51) Int. Cl.
*A01H 5/00* (2006.01)

(52) U.S. Cl. ..... Plt./330
(58) Field of Classification Search ..... Plt./330, Plt./329, 328
See application file for complete search history.

(56) References Cited

PUBLICATIONS

German PBR Application No. PEL 1902 filed Jun. 4, 2003 and withdrawn Oct. 5, 2004 (Copy of German Gazettes dated 1) Jul. 15, 2003—Listing Assigned Application for Protection No. (2 pgs), 2) May 15, 2004—Publishing Proposed Variety Denomination (2 pgs), and 3) Nov. 15, 2004—Listing Withdrawal of Application for Protection (2pgs)).

Canadian PBR Application No, 03–3901 filed Nov. 21, 2003 (Copy of Canadian Plant Varieties Journal dated Jan., 2004 Listing Assigned Application No. (2 pgs).

Community Plant Variety Office (CPVO) No. 2004/1253 filed Jul. 5, 2004 (Copy of Official Gazette of the CPVO dated Oct. 15, 2004 Listing Assigned Applicatoin No. and Variety Denomination (3 pgs).

Fischer 2005 catalogue offering 'Grasalm' (with shipment of plant material available starting Dec., 2004) (3 pgs).

*Primary Examiner*—Kent Bell
(74) *Attorney, Agent, or Firm*—Foley & Lardner LLP

(57) ABSTRACT

A new and distinct cultivar of *geranium* plant named 'Grasalm' particularly characterized by the combined features of deep pink to rose-red, single-type, star-shaped flowers; medium-sized, semi-spherically shaped inflorescence, high above the foliage; medium-sized, robust, fan-shaped leaves with strong zonation; medium to wide, well-branched and dense plant habit; and floriferous with very early spring flowering response.

1 Drawing Sheet

Genus and species of the plant claimed: *Pelargonium zonale* L'Héritier (hybrid).
Variety denomination: 'Grasalm'.

BACKGROUND OF THE INVENTION

The present invention comprises a new and distinct cultivar of *geranium*, botanically known as *Pelargonium zonale,* and hereinafter referred to by the cultivar name 'Grasalm'.

'Grasalm' is a product of a planned breeding program which had the objective of creating new stellar-type *geranium* cultivars in various flower colors, in combination with early flowering, zoned foliage, and about medium sized, rounded and well-branched plant habit.

'Grasalm' originated from a hybridization made by the inventor, Angelika Utecht, in a controlled breeding program in Hillscheid, Germany, in 1999. The female parent was the unpatented commercial variety 'Mark's Elf', characterized by having rose-red, single-type flowers, relatively small, almost spherical flower heads, medium green foliage with strong zonation, and fairly vigorous growth. The male parent of 'Grasalm' was the unpatented plant no. 82-24-1, characterized by pink, single-type flowers, and medium green foliage without zonation.

'Grasalm' was selected as one flowering plant within the progeny of the stated cross by Angelika Utecht in 2000 in a controlled environment in Fuerteventura, Canary Islands, Spain.

The first act of asexual reproduction of 'Grasalm' was accomplished when vegetative cuttings were taken from the initial selection in the fall of 2000 in a controlled environment in Fuerteventura, Spain, by, or under the supervision of, Angelika Utecht.

Horticultural examination of plants grown from cuttings of the plant initiated in May 2001, in Hillscheid, Germany, and continuing thereafter, has demonstrated that the combination of characteristics as herein disclosed for 'Grasalm' are firmly fixed and are retained through successive generations of asexual reproduction.

BRIEF SUMMARY OF THE INVENTION

'Grasalm' has not been observed under all possible environmental conditions. The phenotype may vary significantly with variations in environment such as temperature, light intensity and day length. The following observations, measurements, and comparisons describe plants grown in Hillscheid, Germany, under greenhouse conditions which approximate those generally used in commercial practice.

The following traits have been repeatedly observed and are determined to be basic characteristics of 'Grasalm' in combination distinguish this *germanium* as a new and distinct cultivar:

1. deep pink to rose-red flower color;
2. medium sized, many-flowered inflorescences, high above the foliage;
3. medium sized, fan-shaped leaves with strong zonation;

4. medium or over sized and well-branched plant habit; and
5. very early spring flowering response.

Of the many commercial cultivars known to the present inventor, the most similar in comparison to 'Grasalm' is the parental variety 'Mark's Elf'.

In comparison to 'Mark's Elf', 'Grasalm' has a somewhat less bluish hue of flower color, somewhat wider umbels, but slightly shorter peduncles, and in general smaller plant habit.

BRIEF DESCRIPTION OF THE DRAWING

The accompanying photographic drawing shows typical flower and foliage characteristics of 'Grasalm' with colors being as true as possible with an illustration of this type. The photographic drawing shows a side perspective view of a flowering potted plant of 'Grasalm' with leaves, buds and inflorescences.

DETAILED BOTANICAL DESCRIPTION

The measurements were taken in Hillscheid, Germany, in mid May, 11 weeks after planting of rooted cuttings. The plants were grown in 14 cm pots, they had not been pinched.

In the following description, color references are made to The Royal Horticultural Society Colour Chart. The color values were determined indoors from plants growing in a green-house in May 2003 in Hillscheid, Germany.

Parentage:
- *Male parent.*—Unpatented, hybrid plant no. 82-24-1.
- *Female parent.*—'Mark's Elf', unpatented commercial variety.

Classification: *Pelargonium zonale* L'Hértier (hybrid).
Propagation: Vegetative cuttings.
Inflorescence:
Umbel:
- *Shape.*—Semi-spherical.
- *Average diameter.*—83 mm.
- *Average depth.*—50 mm.
- *Number of flowers and buds per umbel.*—Up to 40 (occasionally even more).

Peduncle:
- *Peduncle length.*—176 mm.
- *Peduncle diameter.*—3–4 mm.
- *Peduncle color.*—Light green, RHS 143 C, occasionally with a slight tinge of yellow-green, RHS 147 B.

Pedicel:
- *Pedicel length.*—26 mm in length, usually with a spur.
- *Pedicel diameter.*—1.5 mm, thin.
- *Pedicel color.*—Mainly grayish-red, RHS 181 A, the base may be yellow-green, RHS 144 A.

Corolla:
- *Average diameter.*—33 mm.
- *Depth.*—8–10 mm.
- *Form.*—Single-type.
- *Shape.*—Star-shaped, with the upper petals longer and narrower than the lower petals.
- *Number of petals.*—5.
- *Number of petaloids.*—None.

Petals:
- *Shape of petals.*—Roughly rhomboid, with the upper petals much narrower than the lower petals; with acute base and acuminate tip, possibly divided.
- *Size of petals.*—Upper petals: 23 mm long, 7 mm wide; lower petals: 18–20 mm long, 9 mm wide.
- *Margin of petals.*—Dentate towards the tip; lower petals: margins near the tips somewhat crenate).
- *Color (general tonality from a distance of three meters).*—Deep pink to rose-red.
- *Color of upper petals.*—Red, RHS 52 A.
- *Markings of upper petals.*—No distinct markings.
- *Color of lower petals.*—Red-purple, intermediate between RHS 57 B and 57 C.
- *Markings of lower petals.*—None.
- *Color of lower surface of petals.*—Upper petals: red, RHS 56 A; lower petals: somewhat red, deeper than RHS 55 A.

Sepals:
- *Color of sepals.*—Upper and lower surfaces: Mainly yellow-green, RHS 144 B; the largest sepal: greyed-red, RHS 179 B, near the bases: greyed-red, RHS 181 B.
- *Number of sepals.*—5.
- *Shape of sepals.*—Ensiform, acute tip, fused base, surface with very short pubescence, margin entire.
- *Size of sepals.*—8 mm long, 4 mm wide for the largest upper sepal, 2–3 mm in width for the other sepals.

Bud (just prior to petals unfolding):
- *Shape.*—Narrow, elliptical.
- *Color of sepals.*—Light green, RHS 144 B.
- *Color of petals.*—More reddish than red-purple hue characterized by RHS 57 B.
- *Length.*—12 mm.
- *Width.*—4–5 mm.

Reproductive organs:
Androecium: 5 fertile anthers, moderate pollen, orange, RHS N25 A, filaments white, RHS 155 D, to light-pink, RHS 52 D.
Gynoecium: One pistil, reddish style and stigma, RHS 46 C, Stigma 5–6-lobed stigma.
Fertility/seed set: Not observed.
Spring flowering response period: In Hillscheid, Germany, in 2003 plants had on average 1.2 flowers opened 9 weeks after planting of rooted cuttings.
Outdoor flower production: Continuously and rich flowering, the flower count in 2003 in Hillscheid, Germany, indicated about 15–20 inflorescences per plant in late summer.
Durability: Good stability of flower color, little fading, good rain resistance.
Lastingness of the individual flower: About 7–8 days at 18° C., about 16 days for the umbel.
Fragrance: None.
Plant:
Foliage:
- *Shape.*—Roughly semi-circular to flabellate, with distinct lobes, respective with incisions and somewhat wavy. No pointed leaf tip, basically semi-circular with lobes. Base truncate or obtuse.
- *Margin.*—Dentate at the tips of lobes, entire towards the base.
- *Texture.*—Upper surface smooth, dull.
- *Size of leaf.*—88 mm wide, 50 mm long.
- *Color of upper surface.*—Medium green, approximately RHS 143 A.
- *Color of zonation.*—Strong, brown, about RHS 200 B.
- *Color of lower surface.*—Green, RHS 143 C.
- *Petioles.*—79–95 mm long, 2.5–3.0 mm diameter, light green in color, approximately RHS 143 B.
- *General appearance and form.*—
- *Stem color.*—Mainly light green, RHS 143 C.

*Internode length.*—15–20 mm.

*Branching pattern.*—9.5 branches.

*Size of plants.*—Height: 15.2 cm, Spread: 26.7 cm (11-week old plants, as described, measured from the top of the soil (base of the main stem) to the surface of the foliage canopy, without inflorescences).

I claim:

1. A new and distinct cultivar of *geranium* plant named 'Grasalm', as described and illustrated herein.

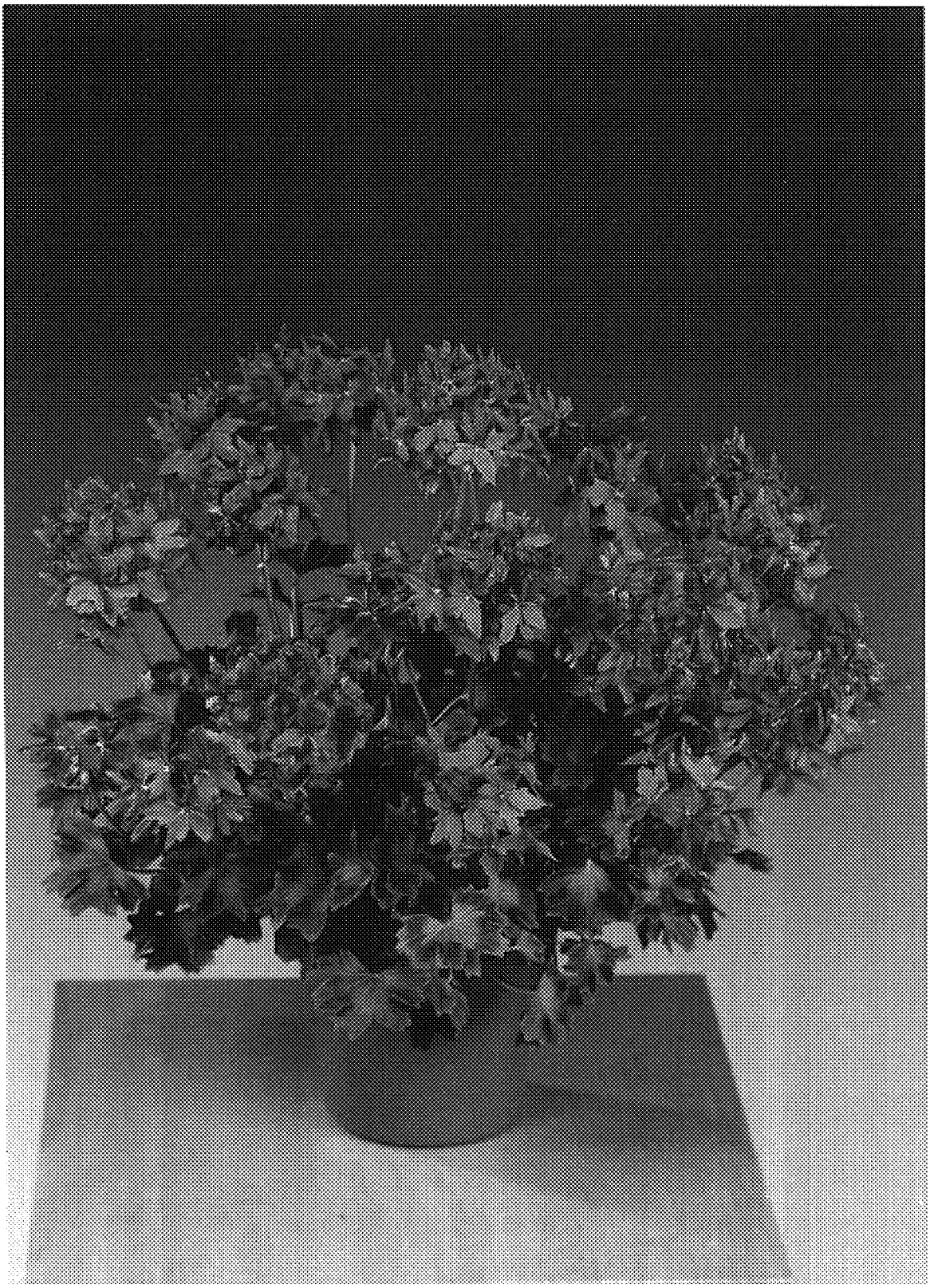

* * * * *